United States Patent [19]

Van Gompel et al.

[11] Patent Number: 4,725,473
[45] Date of Patent: Feb. 16, 1988

[54] CLOTH-LIKE, LIQUID IMPERVIOUS COMPOSITE MATERIAL AND METHOD FOR MAKING THE SAME

[75] Inventors: Paul T. Van Gompel, Hortonville; Karen M. B. Yaccarino, Milwaukee, both of Wis.

[73] Assignee: Kimberly-Clark Corporation, Neenah, Wis.

[21] Appl. No.: 934,582

[22] Filed: Nov. 25, 1986

[51] Int. Cl.$^4$ .......................... A61F 13/16; B32B 7/10; B32B 31/20

[52] U.S. Cl. ................................ 428/156; 128/132 D; 156/73.1; 156/209; 156/219; 156/290; 156/62.6; 156/308.4; 156/309.6; 428/171; 428/172; 428/198; 428/288; 428/296; 428/337; 428/341; 428/903; 604/380

[58] Field of Search .................. 128/132 D; 156/73.1, 156/209, 219, 290, 62.6, 308.4, 309.6; 428/156, 171, 172, 198, 288, 296, 337, 341, 903; 604/380

[56] References Cited

U.S. PATENT DOCUMENTS

| | | |
|---|---|---|
| 2,714,571 | 8/1955 | Irion et al. |
| 3,131,113 | 4/1964 | Arbit et al. |
| 3,622,422 | 11/1971 | Newman ............................. 156/306 |
| 3,622,434 | 11/1971 | Newman . |
| 3,660,200 | 5/1972 | Anderson et al. .................. 156/306 |
| 3,676,242 | 7/1972 | Prentice .............................. 156/62.4 |
| 3,770,534 | 1/1973 | Anselrode .......................... 156/62.2 |
| 4,115,176 | 9/1978 | Ekstrand ........................ 156/244.25 |
| 4,178,407 | 12/1979 | Rubens ................................. 428/284 |
| 4,379,192 | 4/1983 | Wahlquist ............................ 428/156 |
| 4,522,203 | 6/1985 | Mays .................................... 128/132 |

FOREIGN PATENT DOCUMENTS 1185227 3/1970 United Kingdom .

*Primary Examiner*—James C. Cannon
*Attorney, Agent, or Firm*—Douglas L. Miller; Donald L. Traut; Jeremiah J. Duggan

[57] ABSTRACT

The cloth-like, liquid impervious composite material is made by applying a nonwoven layer of loose, unadhered fibers to a liquid impervious film, and then point-bonding the nonwoven layer to the liquid impervious film to form discrete points of adhesion between the fibers and film. Because the fibers in the nonwoven layer are loose and unadhered when applied to the film, the resulting composite material has improved loft and softness. Also, when the composite material is elasticized by an elastic material, it gathers into a more pleasing appearance.

36 Claims, 6 Drawing Figures

CLOTH-LIKE, LIQUID IMPERVIOUS COMPOSITE MATERIAL AND METHOD FOR MAKING THE SAME

BACKGROUND OF THE INVENTION

This invention pertains to a composite material, and more particularly to a liquid impervious composite material having a cloth-like texture on one side thereof and a method for making the same.

Various types of garments are presently available for absorbing human discharge. Examples of these garments include baby diapers, training pants, feminine care products, incontinent garments, and the like. The general structure of these garments include a liquid pervious bodyside liner, an absorbent batt, and a liquid impervious outer cover for containing discharged fluids or solid matter.

One suitable liquid impervious material for use as the outer cover is a thermoplastic film. Although functional as a liquid impervious barrier, it has a characteristic which can be considered undesirable, or even unacceptable, to the wearer. That characteristic is the film's plastic appearance and particularly the plastic feel or texture. In the case of diapers, it may be the mother who objects to the plastic appearance and feel of the diaper against her baby. In the case of training pants for a child or incontinent garments for adults, it is the wearer who will object to the plastic appearance and feel.

Various solutions to this undesirable characteristic of plastic appearance or feel have been pursued. One such attempt is to manufacture the outer cover of a thermoplastic film or composite with a cloth-like texture on the outer surface. One method includes uniformly applying a thin adhesive coating on the surface of a thin film, and then depositing loose filaments on the thin, uniform adhesive layer. Thereafter, the layer of fibers and film may be passed between two nip rolls to insure good adherence between the fibers and film. Although resulting in an article having some cloth-like appearance and texture, the article has less loft and softness than desired, which is probably due to the fact that the fibers are compactly adhered to the film by the layer of adhesive therebetween. In other words, because of the uniform and continuous adhesive layer, there may be too many fibers partially or completely adhered to the film, thereby tending to cause the fibers to lose some of their loft and softness.

Another method, somewhat similar to the above, includes blowing fiber webs onto a thermoplastic film, and then fuse-bonding the layer of fibers and film together by, for example, passing them between heated nip rolls or through some other type of fusion device, such as a heater. The heat causes the surface of the film to become soft and tacky, thereby providing the mechanism for adhering the fibers to the film. Because the total surface of the thermoplastic film provides the necessary adhesive characteristic, the fiber side of the article has less loft and softness than desired.

In another method, loose fibers are blown onto a web or thermoplastic film, and thereafter a liquid binding agent is applied to the fibers and penetrates through the layer of fibers to the film, thereby causing adherence between the fibers and film. If desired, the article can then be passed through a heating or drying device. The resulting article has less loft and softness than those earlier described since the liquid binding agent completely penetrates the layer of fibers resulting in adherence not only between the fibers and film, but also between adjacent fibers due to the running or spreading of the liquid binding agent.

Still another method includes providing a pre-bonded layer of nonwoven fibers, and then meltblowing a plastic onto the pre-bonded fiber layer. The adhesion is provided by the softened and tacky meltblown plastic fibers. Again, the resulting article has less than desired loft and softness due to the meltblowing process and also due to the layer of fibers having been pre-bonded prior to the meltblowing step.

Similar to the just-described method, a pre-bonded layer or web of fibers may have a plastic film coated or extruded thereon. As with the above method, the extruded film adheres not only to the points of density in the fiber layer where the fibers are pre-bonded, but also to points of the fibers between these points of pre-bond density.

Another problem associated with the lack of desired loft and softness occurs when providing a portion of the article with an elasticized opening, such as a waist or leg opening. Upon relaxing the elastic after it has been attached to the article in its stretched state, it gathers that portion of the article to which it is attached. It is naturally desirable not only to provide good elasticity about the opening, but also a pleasing appearance by the gathered portion of the article. Because of the lack of desired loft and softness of the above-described cloth-like articles, they generally do not uniformly gather into the desired pleasing appearance. This is due in part by the slight stiffness of the article caused by the methods of adhering the loose fibers to the film, as earlier described above.

Thus, the need exists for an improved cloth-like, liquid impervious article that has better loft and softness characteristics, and which presents a pleasing gathered appearance upon being elasticized.

SUMMARY OF THE INVENTION

The present invention provides an improved cloth-like, liquid impervious composite material having good loft and softness, and which upon being gathered by an elastic presents a more uniform and pleasing gathered appearance. The composite material can be used as the outer cover in garments such as baby diapers, child's training pant, incontinent garments, and the like.

In one form of the invention, there is provided a method for making a cloth-like, liquid impervious composite material comprising the steps of providing a liquid impervious film; applying a nonwoven layer of loose, unadhered fibers to the liquid impervious film to form a cloth-like surface thereon; and then point-bonding the nonwoven layer of loose, unadhered fibers to the liquid impervious film to form discrete points of adhesion between fibers and film, thereby forming a liquid impervious composite material having a cloth-like texture on one surface thereof.

In another form of the invention, there is provided a cloth-like, liquid impervious composite material made by the method of providing a liquid impervious film; applying a nonwoven layer of loose, unadhered fibers to the liquid impervious film; and then point-bonding the nonwoven layer of loose, unadhered fibers to the film to form discrete points of adhesion between the fibers and film.

In yet another form of the present invention, there is provided a cloth-like, liquid impervious composite material comprising a liquid impervious film having opposite surfaces and made of a polymeric material, a nonwoven layer of loose, unadhered fibers disposed on one of the surfaces to provide a cloth-like texture to the surface, and a plurality of bond points discretely adhering points of the liquid impervious film to respective points of the nonwoven layer. Each bond point has an area between about 0.05 to about 1.5 mm$^2$, and is spaced from adjacent bond points between about 0.5 to about 4.0 mm. The bond points have a cumulative area between about 5% to about 50% of the area of the mutually facing surfaces of the liquid impervious film and the nonwoven layer.

Further objects of the present invention will appear in the description hereafter.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein.

DESCRIPTION OF A PREFERRED EMBODIMENT

Figure 1:
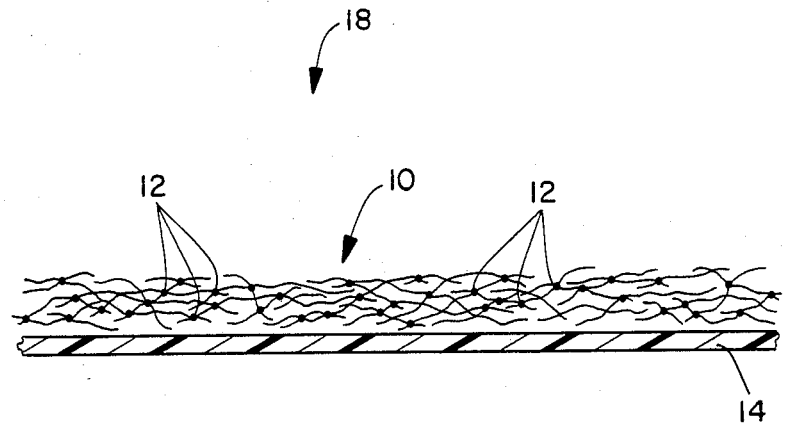
FIG. 1 is an elevational view of a prior art article with a pre-bonded layer of fibers slightly spaced from a base film.
Figure 2:
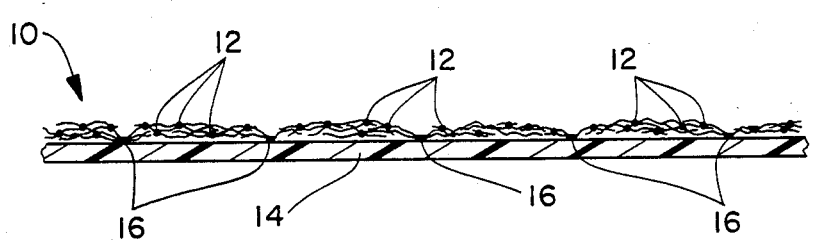
FIG. 2 is an elevational view of the prior art article in FIG. 1 after the pre-bonded layer of fibers has been adhered to the base film.

Referring to FIGS. 1 and 2, a prior art article is illustrated. In FIG. 1, pre-bonded layer of fibers 10 is slightly spaced above a base film 14, which can be made of any suitable material such as a polymer. Pre-bonded layer 10 includes a plurality of preformed bond points 12 to adhere the fibers together.

FIG. 2 illustrates pre-bonded layer 10 adhered to base film 14 at bond points 16. Bond points 16 are applied in any conventional manner. As illustrated in FIG. 2, the prior art article has somewhat less than desired loft and softness due to the number of bond points 12, 16. Although bond points 16 are necessary to adhere the fibers of pre-bonded layer 10 to base film 14, the additional bond points 12 forming pre-bonded layer 10 are undesirable since they add additional points of density in the pre-bonded layer 10. These additional points of density formed by bond points 12 cause the article to have less loft and less softness than desired.

In addition, because of the increased number of points of density causes by bond points 12, the prior art article is somewhat more stiff than desired. Consequently, upon applying a stretched elastic to the article and then relaxing the attached elastic, the article tends to gather in a less than pleasing manner. This stiffness can also serve to degrade prematurely the elastic characteristics of the attached elastic.

Although FIGS. 1 and 2 illustrate a pre-bonded layer 10 bonded to base film 14 by bond points 16, pre-bonded layer 10 may also be adhered to base film 14 by use of a liquid binding agent or by heating base film 14 so that its surface becomes soft and tacky. In either case, the resulting article would have similar undesirable characteristics.

Figure 3:
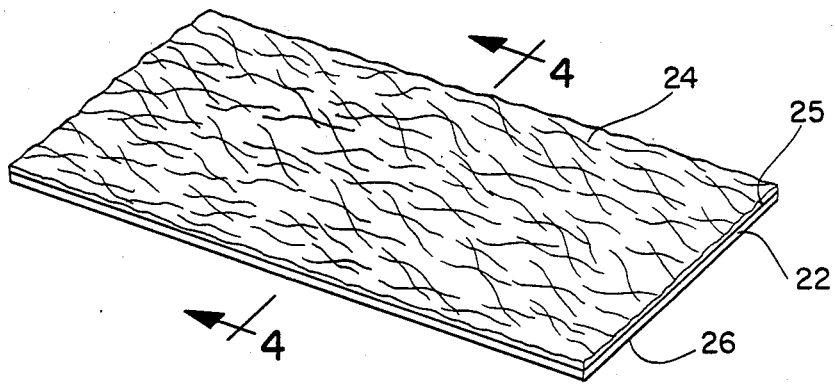
FIG. 3 is a perspective view of a preferred embodiment of the present invention before the nonwoven layer of loose, unadhered fibers have been point-bonded to the film.
Figure 4:
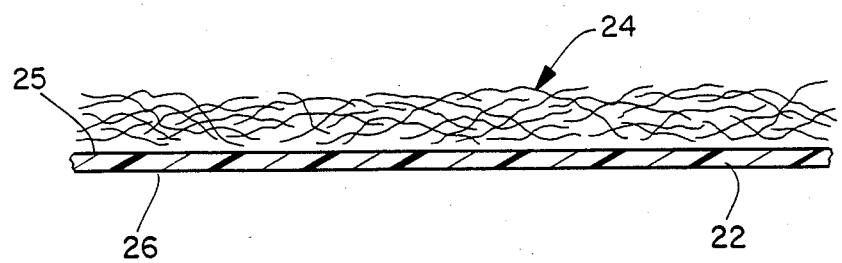
FIG. 4 is a sectional view of FIG. 3 taken along line 4—4 and viewed in the direction of the arrows.
Figure 5:
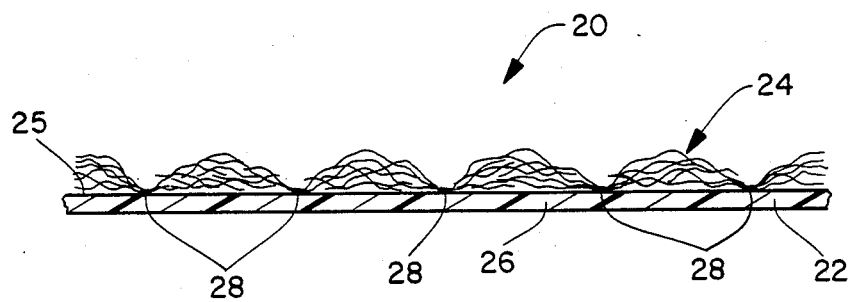
FIG. 5 is a view similar to FIG. 4 with the nonwoven layer of loose, unadhered fibers point-bonded to the film.

Referring to FIGS. 3-5, there is illustrated an improved cloth-like, liquid impervious composite material 20 according to the present invention, which can be used as the outer cover of garments for absorbing human discharge. FIG. 3 illustrates liquid impervious film 22 having lightly deposited thereon nonwoven layer 24 of loose, unadhered fibers. The term "unadhered" means that the individual fibers are loose and free of any binding agent when lightly deposited on top surface 25 of film 22. Nonwoven layer 24 provides the cloth-like texture, and bottom surface 26 of film 22 provides the liquid impervious side of composite material 20.

Film 22 may be made of any suitable polymeric material, such as polypropylene or polyethylene. Film 22 may be also a copolymer such as ethylene methylacrylate, ethylene vinylacetate, or ethylvinylacrylate, and film 22 can also be made of co-extruded films of these materials or blends thereof.

Film 22 can have a thickness in the range between about 0.3 to about 6.0 mils, and preferably a thickness range between about 0.3 to about 2.0 mils. An optimum thickness of film 22 is a range between about 0.5 to about 1.0 mils.

The fibers of nonwoven layer 24 may be made of any thermoplastic material, such as polypropylene, polyethylene, polyester, blends thereof, or blends with chisso; chisso being a bi-component fiber having a polypropylene core and a polyethylene sheath. These fibers may be of any length or denier as a function of the particular material or blends of material.

Nonwoven layer 24 can have a basis weight in the range between about 10 to about 50 gsm, and preferably a basis weight range between about 15 to about 30 gsm. The optimum basis weight range is between about 20 to about 25 gsm.

Referring to FIG. 5, nonwoven layer 24 is adhered to film 22 by a plurality of discrete bond points 28 bonding the individual fibers to film 22. As illustrated, these discrete bond points 28 can be uniformly applied, as will be described in greater detail below. It can be appreciated that since nonwoven layer 24 is not pre-bonded, such as pre-bonded layer 10, and since nonwoven layer 24 is not adhered by a liquid binding agent or by heating film 22 to become soft and tacky, that nonwoven layer 24 has better loft and softness. This is due primarily to the elimination of the type of bond points 12 in the prior art article in FIGS. 1 and 2. Thus, by bonding discrete points of nonwoven layer 24 to respective discrete points of film 22, fewer bond points 28 are needed in contrast to the prior art article, thereby resulting in fewer points of density. This also results in the better loft and softness provided by nonwoven layer 24. Even though fewer bond points exist in composite material 20, there is good adhesion between nonwoven layer 24 and film 22 provided not only by bond points 28, but also by the mechanical entanglement of individual fibers.

Because of the improved loft and softness of composite material 20 of the present invention, a stretched elastic attached to composite material 20 will elasticize the material in a more pleasing gathered configuration. Also, because of the improved flexibility due to the better loft and softness, composite material 20 will not prematurely degrade the elastic characteristics.

Figure 6:
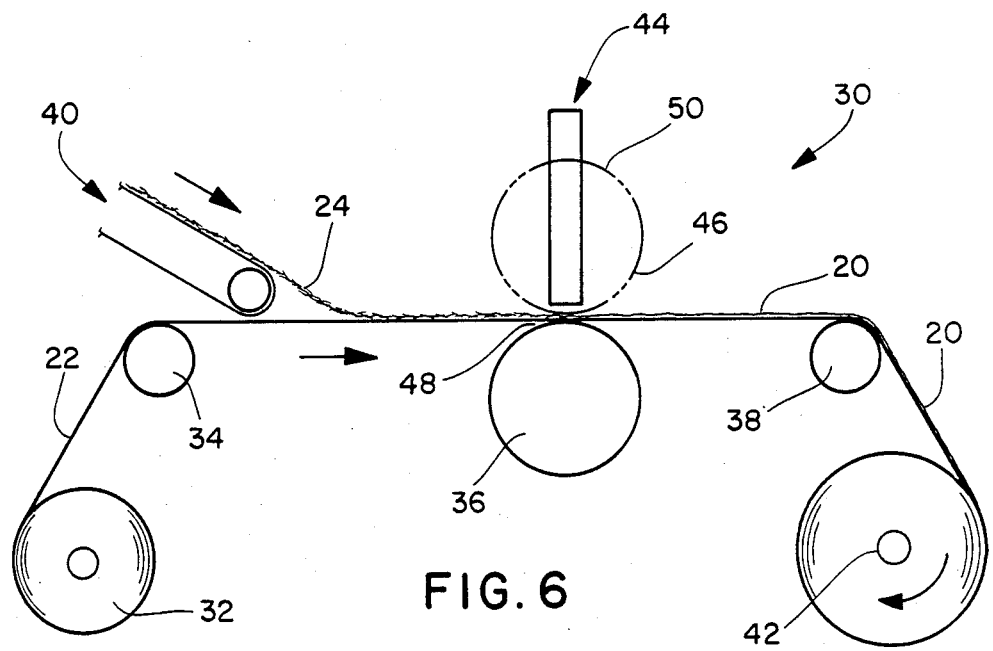
FIG. 6 is a schematic of an assembly which may be operated according to one embodiment of the present invention.

Referring to FIG. 6, apparatus 30 is schematically illustrated for practicing the method of the present invention. Apparatus 30 comprises a supply 32 of film 22 that is moved along rolls 34, 36, 38. Carding machine 40 applies the fibers of nonwoven layer 24 to film 22, and at roll 36, nonwoven layer 24 and film 22 are adhered together by discrete bond points 28. Composite material 20 is then moved over roll 38 and taken up by spool 42. The fibers of layer 24 can also be applied by meltblowing, spinning, or other suitable nonwoven apparatus.

Since the fibers of nonwoven layer 24 are loose and unadhered when bonded to film 22, and since it is necessary that nonwoven layer 24 and film 22 have good adhesion therebetween, the dimensions of each bond point 28 are important to the present invention. Thus, the area of each bond point is between about 0.05 to about 1.5 mm$^2$, and the distance between bond points 28 is between about 0.5 to about 4.0 mm. The cumulative area of all the bond points 28 is between about 5% to about 50% of the area defined by the mutually facing surfaces of nonwoven layer 24 and film 22.

If increased adherence between nonwoven layer 24 and film 22 is desired, then the area of each bond point 28 is preferably between about 0.09 to about 0.56 mm$^2$, and optimally between about 0.15 to about 0.30 mm$^2$. The distance between adjacent bond points 28 is then preferably between about 0.90 to about 1.50 mm, and optimally between about 1.1 to about 1.30 mm. The cumulative area of all bond points 28 is then preferably between about 5% to about 30% of the mutually facing area between layer 24 and film 22, and optimally between about 8% to about 15%.

The discrete bonding between nonwoven layer 24 and film 22 can be provided by ultrasonic bonder 44, wherein roll 36 also serves as an anvil for the ultrasonic bonding.

Alternatively, bonding can be provided by embossing roll 46 indicated in phantom lines in FIG. 6, and which forms a gap or nip 48 with roll 36. Embossing roll 46 can be provided with a pattern of upstanding projections (not shown) which penetrate through nonwoven layer 24 to film 22 to create the discrete bond points 28. If desired, embossing roll 46 and roll 36 can be heated. For example, embossing roll 46 can be heated to a temperature between about 100° to about 300° F., preferably between about 175° to 275° F., or optimally between about 200° to 250° F. Roll 36 can be heated to a temperature between about 100° to about 225° F., preferably between about 125° to about 175° F., or optimally between about 140° to about 160° F.

Also if desired, the pressure at nip 48 can be varied. For example, the nip pressure can be between about 0 to about 80 psi, preferably between about 5 to about 40 psi, or optimally between about 10 to about 20 psi.

In another alternate means of bonding, print roll 50, which is indicated by the same phantom lines used in describing embossing roll 48, has a pattern of upstanding projections thereon and a means (not shown) for applying adhesive only to the projections. Upon moving nonwoven layer 24 and film 22 between print roll 50 and roll 36, the projections (not shown) on print roll 50 penetrate through nonwoven layer 24 to film 22, thereby creating the discrete bond points 28. In this method of bonding, there is no necessity of having temperature compatability between the materials of nonwoven layer 24 and the materials of film 22.

Yet another means of bonding includes the use of powder binding agents. The use of powder binders can be incorporated as binding agents during a thermal bonding process, using lower temperatures and pressures, rather than using the melt properties of the nonwoven or film. For example, powder binding agents can be used in polypropylene and polyester carded webs.

While this invention has been described as having a preferred embodiment, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. A method for making a cloth-like, liquid impervious composite material, comprising the steps of:
   providing a liquid impervious film as a carrier sheet,
   depositing loose, unadhered fibers that are free of any bonding between individual fibers to the liquid impervious film to form a cloth-like nonwoven surface thereon, and
   point-bonding the deposited loose, unadhered fibers to the liquid impervious film to form discrete points of bonding between the fibers and film, thereby forming a cloth-like liquid impervious composite material having good loft and softness.

2. The method of claim 1 wherein the step of point-bonding is performed by an ultrasonic bonding device.

3. The method of claim 1 wherein the step of point-bonding is performed by a pair of thermal embossing rolls, one of the rolls having a pattern of discrete upstanding bond points thereon.

4. The method of claim 3 wherein said one roll is maintained at a temperature between about 100° F. to about 300° F., and the other roll is maintained at a temperature between about 100° F. to about 225° F., and the nip pressure between the rolls is between about 0 to about 80 psi.

5. The method of claim 4 wherein the temperature of said one roll is preferably between about 175° F. to about 275° F., the temperature of the other roll is preferably between about 125° F. to about 175° F., and the nip pressure is preferably between about 5 to about 40 psi.

6. The method of claim 5 wherein the temperature of said one roll is optimally between about 200° F. to about 250° F., the temperature of the other roll is optimally between about 140° F. to about 160° F., and the nip pressure is optimally between about 10 to about 20 psi.

7. The method of claim 1 wherein the step of point-bonding is performed by a print adhesive roll.

8. The method of claim 1 wherein the step of point-bonding is performed by a pair of embossing rolls, one of the rolls having a pattern of powder binding agent thereon.

9. The method of claim 1 wherein the loose, unadhered fibers are made of a polymeric material.

10. The method of claim 9 wherein the polymeric material is polypropylene, polyethylene, polyester, or blends thereof.

11. The method of claim 10 wherein the polymeric material includes chisso.

12. The method of claim 1 wherein the loose, unadhered films are made of a copolymeric material.

13. A cloth-like, liquid impervious composite material made by the method comprising the steps of:
   providing a liquid impervious film as a carrier sheet,
   depositing loose, unadhered fibers that are free of any bonding between individual fibers to the liquid impervious film to form a cloth-like nonwoven surface thereon, and
   point-bonding the deposited loose, unadhered fibers to the liquid impervious film to form discrete points of bonding between the fibers and film.

14. The composite material of claim 13 wherein the point-bonding is performed by an ultrasonic device.

15. The composite material of claim 13 wherein the point-bonding is performed by a pair of thermal embossing rolls, one of the rolls having a pattern of discrete upstanding bond points thereon.

16. The composite material of claim 13 wherein the point-bonding is performed by a print adhesive roll.

17. The composite material of claim 13 wherein the deposited fibers as a nonwoven layer have a basis weight between about 10 to about 50 gsm.

18. The composite material of claim 17 wherein the nonwoven layer basis weight is preferably between about 15 to about 30 gsm.

19. The composite material of claim 18 wherein the nonwoven layer basis weight is optimally between about 20 to about 25 gsm.

20. The composite material of claim 13 wherein the film has a thickness between about 0.3 to about 6.0 mils.

21. The composite material of claim 20 wherein the film thickness is preferably between about 0.3 to about 2.0 mils.

22. The composite material of claim 21 wherein the film thickness is optimally between about 0.5 to about 1.0 mils.

23. A cloth-like, liquid impervious composite material, comprising:
   a liquid impervious film having opposite surfaces,
   loose, unadhered fibers disposed on one of said surfaces to provide a cloth-like nonwoven layer on said one surface, and
   a plurality of bond points discretely bonding points of said liquid impervious material to respective points said nonwoven layer,
   each said bond point having an area between about 0.05 to about 1.5 mm$^2$,
   said bond points being individually spaced apart between about 0.5 to about 4.0 mm,
   said bond points having a cumulative area between about 5% to about 50% of the area of mutually facing surfaces of said liquid impervious film and said nonwoven layer.

24. The composite material of claim 23 wherein each said bond point area is preferably between about 0.09 to about 0.56 mm$^2$,
   said bond points are individually spaced apart preferably between about 0.90 to about 1.50 mm, and
   said bond points have a cumulative area preferably between about 5% to about 30% of the area of said mutually facing surfaces.

25. The composite material of claim 24 wherein each said bond point area is optimally between about 0.15 to about 0.30 mm$^2$,
   said bond points are individually spaced apart optimally between about 1.1 to about 1.30 mm, and
   said bond points have a cumulative area optimally between about 8% to about 15% of said mutually facing surfaces.

26. The composite material of claim 23 wherein said film has a thickness between 0.3 to about 6.0 mils.

27. The composite material of claim 26 wherein said film thickness is preferably between about 0.3 to about 2.0 mils.

28. The composite material of claim 27 wherein said film thickness is optimally between about 0.4 to about 1.0 mils.

29. The composite material of claim 23 wherein said nonwoven layer has a basis weight between about 10 to about 50 gsm.

30. The composite material of claim 29 wherein said nonwoven layer basis weight is preferably between about 15 to about 30 gsm.

31. The composite material of claim 30 wherein said nonwoven layer basis weight is optimally between about 20 to about 25 gsm.

32. The composite material of claim 23 wherein said film is made of a polymeric material.

33. The composite material of claim 23 wherein said loose, unadhered fibers are made of a polymeric material.

34. The composite material of claim 33 wherein said fiber polymeric material is polypropylene, polyethylene, polyester, or blends thereof.

35. The composite material of claim 34 wherein said fiber polymeric material includes chisso.

36. The composite material of claim 23 wherein said film is made of a copolymeric material.

* * * * *

UNITED STATES PATENT AND TRADEMARK OFFICE
CERTIFICATE OF CORRECTION

PATENT NO. : 4,725,473
DATED : February 16, 1988
INVENTOR(S) : Paul T. Van Gompel and Karen M. B. Yaccarino It is certified that error appears in the above-identified patent and that said Letters Patent is hereby corrected as shown below:

Column 7, line 4, delete "films" and substitute therefor --fibers--.

Signed and Sealed this

Twenty-sixth Day of December, 1989

*Attest:*

JEFFREY M. SAMUELS

*Attesting Officer*      *Acting Commissioner of Patents and Trademarks*